(12) United States Patent
Yang et al.

(10) Patent No.: US 8,133,853 B1
(45) Date of Patent: Mar. 13, 2012

(54) FRAGRANCED SOAP COMPOSITIONS

(75) Inventors: Lin Yang, Woodbridge, CT (US); Liang Sheng Tsaur, Norwood, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 12/891,874

(22) Filed: Sep. 28, 2010

(51) Int. Cl.
C11D 3/50 (2006.01)

(52) U.S. Cl. ....................... 510/101; 510/481

(58) Field of Classification Search ................ 510/101, 510/481
See application file for complete search history.

(56) References Cited

U.S. PATENT DOCUMENTS

| | | | |
|---|---|---|---|
| 4,486,328 A | 12/1984 | Knott et al. | |
| 4,975,218 A | 12/1990 | Rosser | |
| 5,147,574 A | 9/1992 | MacGilp et al. | |
| 5,308,526 A | 5/1994 | Dias et al. | |
| 5,312,559 A | 5/1994 | Kacher et al. | |
| 5,540,853 A * | 7/1996 | Trinh et al. ................ | 510/101 |
| 5,767,059 A | 6/1998 | Umemoto et al. | |
| 5,851,978 A | 12/1998 | Shana'a | |
| 6,812,192 B2 | 11/2004 | Ribery et al. | |
| 6,852,681 B1 * | 2/2005 | Kerschner et al. ............ | 510/152 |
| 6,906,016 B1 | 6/2005 | Tsaur | |
| 7,015,179 B1 | 3/2006 | Massaro et al. | |
| 2005/0003975 A1 * | 1/2005 | Browne et al. ................ | 510/101 |
| 2005/0020461 A1 | 1/2005 | Seki | |
| 2005/0220736 A1 | 10/2005 | Polonka et al. | |
| 2008/0108542 A1 * | 5/2008 | Perring et al. .................... | 512/4 |

FOREIGN PATENT DOCUMENTS

| | | |
|---|---|---|
| DE | 102005008837 A1 | 2/2005 |
| EP | 1516917 A1 | 3/2005 |
| EP | 2218438 A1 | 8/2010 |
| GB | 2 351 979 | 1/2001 |
| WO | 95/13355 | 5/1995 |
| WO | 96/36313 | 11/1996 |
| WO | 97/27279 | 7/1997 |

OTHER PUBLICATIONS

Co-Pending U.S. Appl. No. 12/891,879, Tsaur, filed Sep. 28, 2010, entitled: Liquid Soap Compositions.
International Search Report PCT/EP2011/063902 dated Nov. 18, 2011.

* cited by examiner

*Primary Examiner* — John Hardee
(74) *Attorney, Agent, or Firm* — Milton L. Honig

(57) ABSTRACT

A personal care composition is provided which includes a fragrance component selected from the group consisting of hexyl acetate, dihydromyrcenol, phenyl ethyl alcohol, benzyl acetate and mixtures thereof, and from 1 to 30% of a $C_{10}$-$C_{24}$ fatty acid material by weight of the composition, wherein from 60 to 85% by weight of the fatty acid material is a salt and a remainder of the fatty acid material is a free fatty acid.

7 Claims, No Drawings

FRAGRANCED SOAP COMPOSITIONS

BACKGROUND OF THE INVENTION

1. Field of the Invention

The invention concerns liquid and bar soap compositions with enhanced fragrance properties.

2. The Related Art

Soap is a chemical term for salts of $C_{10}$-$C_{24}$ fatty acids. Personal care compositions such as, but not limited to, liquid cleansers, toilet bars, shampoos, shaving compositions and deodorant/antiperspirant formulas may incorporate substantial amounts of soap. The fatty acid raw material invariably includes some small amount of lower molecular weight acids. These may be $C_4$-$C_8$ acids. These present a malodor issue.

Short chain acids are volatile. It takes very little of these materials to have a large negative sensorial impact. For instance, hexanoic acid (caproic acid) has the odor of limburger cheese. Butyric acid is described as simply having an obnoxious odor. For these reasons, soap containing formulations require odor masking compounds and/or a cover of pleasant fragrance emitting substances.

Representative disclosures of soap formulations are herein described. U.S. Pat. No. 5,147,574 (MacGilp et al.) disclose liquid dispersoidal cleansing compositions including 5-20% saturated higher fatty acid potassium soap, 3-18% of free fatty acids, wherein the soap and free fatty acids have a ratio of about 1:0.5 to 1:1.

U.S. Pat. No. 5,308,526 (Dias et al.) reports a stable mild dispersoidal liquid soap having 5-20% potassium $C_8$-$C_{22}$ fatty acid soap, 0.1-7% of $C_8$-$C_{22}$ free fatty acid, 35-70% water and a polyol, petrolatum and glycol ester.

U.S. Pat. No. 5,312,559 (Kasher et al.) reports a mild soap personal cleansing and moisturizing composition including $C_3$-$C_{22}$ free fatty acid soap, $C_8$-$C_{22}$ free fatty acid, water and emollients.

U.S. Pat. No. 5,851,978 (Shana'a) reports an aqueous cleansing and moisturizing composition that includes 5-35 weight % of $C_8$-$C_{22}$ fatty acid and up to 10 weight % of a surface active agent.

U.S. Pat. No. 6,906,016 B1 (Tsaur) details liquid cleansers which comprise a water soluble or water swellable starch combined with linear $C_8$-$C_{13}$ fatty acids.

U.S. Patent Application Publication 2005/0020461 A1 (Seki) describes a cleansing composition with 20-50% of fatty acids and salts thereof, wherein the content of fatty acids having 20-24 carbon atoms is from 10-30% by weight of the total fatty acid components, and a weight ratio of fatty acids having not more than 15 carbon atoms to fatty acids having not less than 16 carbon atoms is in a range from 20:80 to 50:50.

Finally, U.S. Patent Application Publication 2005/0220736 A1 (Polonka et al.) reports partially neutralized fatty acids in compositions that deliver enhanced visual benefits to the skin with specific optical attributes. Most of the aforementioned patent documents disclose use of a perfume (fragrance) in the compositions.

Fragrances can be quite expensive, and since they are a mixture of many components, it is difficult to know which have the best suppressant effect against short chain fatty acid malodor. It would be useful to combine the most appropriate soap base with the most efficient fragrance component(s) to achieve the most cost effective and best aesthetic result.

SUMMARY OF THE INVENTION

A personal care composition is provided which includes:
(i) from 0.00001 to 1% by weight of the composition of a fragrance component selected from the group consisting of hexyl acetate, dihydromyrcenol, phenyl ethyl alcohol, benzyl acetate and mixtures thereof; and
(ii) from 1 to 30% of a $C_{10}$-$C_{24}$ fatty acid material by weight of the composition, wherein from 60 to 85% by weight of the fatty acid material is a salt and a remainder of the fatty acid material is a free fatty acid.

DETAILED DISCUSSION OF THE INVENTION

Now it has been found that certain fragrance components release relatively rapidly from a soap formulated personal care composition. Rapid release further requires a $C_{10}$-$C_{24}$ fatty acid material wherein from 50 to 65% by weight of the material is a salt of the fatty acid (i.e. a soap) and any remaining material is free fatty acid.

The fragrance component will be present in amounts from 0.00001 to 1%, preferably from 0.0001 to 1%, more preferably from 0.001 to 0.5%, and optimally from 0.05 to 0.2% by weight of the composition. Suitable fragrance components may be selected from the group consisting of hexyl acetate, dihydromyrcenol, phenyl ethyl alcohol, benzyl acetate and mixtures thereof. Particularly preferred fatty acid materials are those selected from the group consisting of lauric acid, myristic acid, stearic acid, palmitic acid and mixtures thereof. Amounts of the fatty acid material may range from 1 to 30%, preferably from 5 to 20%, and optimally from 10 to 15% by weight of the composition.

Amounts of the fatty acid material which is present in salt form may range from 60 to 85%, preferably from 60 to 80%, more preferably from 65 to 85%, and optimally from 70 to 80% by weight of the fatty acid material.

Counterions to the fatty acids when in salt form may be but are not limited to sodium, potassium, ammonium and triethanolammonium cations. Particularly preferred are the sodium salts.

One method of obtaining salts is to formulate fatty acids into the composition. At a subsequent time, the composition in fluidized form may be neutralized by addition of an alkali metal hydroxide such as sodium hydroxide or potassium hydroxide in an aqueous solution and thereby form the respective sodium or potassium fatty acid salts.

Compositions of this invention may exhibit a range of pH. Particularly preferred, but not limiting, is a pH which may range from 7.5 to 9, preferably from 7.5 to 8.5, and optimally from 7.7 to 8.5.

Advantageously the soap may be present as the major surfactant of the composition. Often the compositions may include a further surfactant(s). Co-surfactants may be anionic, nonionic, cationic or amphoteric type. Amounts of the co-surfactant may range from 0.1 to 15%, preferably from 1 to 10%, and optimally from 3 to 7% by weight of the composition.

Examples illustrative of anionic co-surfactants include alkyl sulfates, alkyl ether sulfates, alkyl glycerol ether sulfonates, alkyl sulfonates, sulfonated fatty esters, sulfonated fatty acids, acyl sarcosinates, methyl acyl taurates, N-acyl glutamates, acyl isethionates, alkyl sulfosuccinates, alkyl phosphates esters, ethoxylated alkyl phosphate esters, trideceth sulfates and mixtures thereof.

Nonionics suitable as co-surfactants include compounds produced by the condensation of alkylene oxide groups with organic hydrophobic compounds which may be aliphatic or alkyl aromatic. Illustrative are polyethylene oxide condensates of alkyl phenols, condensation products of ethylene oxide with a product resulting from reaction of propylene oxide and ethylene diamine, condensation products of aliphatic alcohols having $C_8$-$C_{18}$ carbon atoms with 10-30 moles of ethylene oxide per mole of alcohol, alkyl polyglucosides and mixtures thereof. Also suitable may be teritiary amine oxides such as dimethyl dododecylamine oxide and oleyl di(2-hydroxyethyl) amine oxide.

Suitable amphoteric surfactants include betaines. Among this group are alkyl betaines such as lauryl dimethyl carboxymethyl betaine and cocamidopropyl betaine.

Suitable cationic co-surfactants include stearyl dimethylbenzyl ammonium chloride, dodecyl trimethylammonium chloride, stearalkonium chloride and ditallow (hydrogenated) dimethyl ammonium chloride.

The personal care compositions may include a structuring system, particularly for liquid compositions. Starches are particularly useful for this purpose. Typical starches are polysaccharides derived from plants such as corn, waxy corn, tapioca, potato, wheat or rice starches. These may be native, derivatized and/or hydrolyzed. The modified variety may have hydrophilic ionic and/or nonionic groups such as phosphate, sulfate, sulfonate, carboxylate or hydroxypropyl groups. Particularly preferred is tapioca starch and the chemically modified starch known was PureGel B990 available from the Grain Processing Company (sodium hydroxypropyl starch phosphate). Amounts of the structuring agent may range from 0.01 to 10%, preferably from 0.1 to 5%, and more preferably from 2 to 4% by weight of the composition.

Polyols may also be utilized for structuring. Illustrative are the polyoxyethylene glycols (PEG) and polyoxypropylene glycol (PPG) condensates. Especially useful are those condensates of number average molecular weight ranging from 1000 to 100,000, preferably from 5000 to 75,000, and more preferably from 40,000 to 50,000. Illustrative is PEG 45M. Amounts of the polyol structurants may range from 0.001 to 5%, particularly from 0.01 to 1%, and especially from 0.02 to 0.5% by weight of the composition.

Additionally, the personal care compositions may include deposition aids. Most often these substances are cationic polymers. Illustrative are the cationic guar gums such as Jaguar® C13S, cationic modified cellulose such as Polymer® JR30, and synthetic cationic polymers such as Merquat 550®.

Other components of the personal care compositions may include sequestering agents such as tetrasodium ethylene diamine tetraacetate, coloring agents, opacifiers, pearlizers, foam boosters (such as cocamido monoethanolamide), electrolytes (such as sodium chloride or sodium sulfate), antioxidants (such as butylated hydroxy toluene), antimicrobials (such as 2-hydroxy-4,2',4'-trichlorodiphenylether) and preservatives (such as methyl paraben and propyl paraben, Kathon CG® and Glydant Plus®).

Compositions of this invention may be in bar or liquid form. In most instances, water will be present which may range from 0.5 to 90%, in some instances from 10 to 85%, and in other instances from 50 to 80% by weight of the personal care compositions.

All documents referred to herein, including all patents, patent applications, and printed publications, are hereby incorporated by reference in their entirety in this disclosure.

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

It should be noted that in specifying any range of concentration or amount, any particular upper concentration can be associated with any particular lower concentration or amount.

EXAMPLE 1

A series of liquid soap compositions were formulated. The compositions are detailed under Table I. The fatty acids of lauric, myristic and stearic/palmitic acids were neutralized in situ by reaction with sodium hydroxide. For instance, Example 1 with 60% degree of neutralization contains about 6.6% sodium fatty acid and about 4.9% free fatty acid.

TABLE I

| Chemical Name | Example (Weight %) | | | |
|---|---|---|---|---|
| | 1 | 2 | 3 | 4 |
| Cocamidopropyl Betaine | 6 | 6 | 6 | 6 |
| Lauric Acid | 8.5 | 8.5 | 8.5 | 8.5 |
| Myristic Acid | 2 | 2 | 2 | 2 |
| Stearic/Palmitic Acids | 1 | 1 | 1 | 1 |
| B990 Starch | 3.5 | 3.5 | 3.5 | 3.5 |
| Fragrance | 1 | 1 | 1 | 1 |
| PEG 45M | 0.06 | 0.06 | 0.06 | 0.06 |
| Water | Balance | Balance | Balance | Balance |
| Degree of Neutralization with Sodium Hydroxide | 60% | 70% | 80% | 96% |
| pH (neat) | 7.86 | 8.26 | 8.41 | 9.25 |
| pH (10X diluted) | 8.43 | 8.69 | 8.78 | 9.47 |

Fragrance analysis of headspace over the samples and 10× water diluted samples was performed as follows. Gas chromatography (GC) was utilized to identify fragrance components and their relative amounts in the headspace. The samples were also mixed with distilled water at a 1 to 9 weight ratio, and placed on a stirring plate for 2 to 3 hours. Then 2 grams of the diluted sample was weighed into a GC vial to test for the odor impact. All GC samples were left at room temperature for at least 12 hours before GC measurement to ensure equilibrium of fragrance in the headspace. There was no incubation (all experiments were done at room temperature) for these samples during GC measurement. Error limits are +/−0.05 for values in Tables II and III.

Normalized headspace of relative weight amounts of each fragrance component was charted and is reported in Table II. This headspace represents fragrance distribution over the soap compositions held within a typical product bottle as found on a shelf of a store. Sample 4 is utilized as the comparative control with normalized 1.00 value against which all the other samples are evaluated. In the bottle before use, sample 4 provides the strongest scent.

TABLE II

| Fragrance Component | Example | | | |
|---|---|---|---|---|
| | 1 | 2 | 3 | 4 |
| Alpha-Pinene | 0.80 | 0.87 | 0.95 | 1.00 |
| Beta-Pinene | 0.73 | 0.77 | 0.86 | 1.00 |
| Hexyl Acetate | 0.90 | 0.76 | 0.87 | 1.00 |
| Limonene | 0.57 | 0.60 | 0.75 | 1.00 |
| Dihydromyrcenol | 0.62 | 0.49 | 0.55 | 1.00 |
| Phenyl Ethyl Alcohol | 0.59 | 0.47 | 0.44 | 1.00 |
| Benzyl Acetate | 0.80 | 0.64 | 0.63 | 1.00 |
| Citronellol | 0.49 | 0.40 | 0.52 | 1.00 |
| Lilial | 0.48 | 0.40 | 0.55 | 1.00 |

Most important for the present problem and invention was to identify fragrance components capable of blooming during actual use of the product. For shampoos, body wash and hand cleansers, blooming is critical condition for the circa 10 times dilution with water as used by the consumer. Results as normalized headspace of each fragrance component over a 10× diluted solution of each Sample is reported in Table III.

TABLE III

| Fragrance Component | Example | | | |
|---|---|---|---|---|
| | 1 | 2 | 3 | 4 |
| Alpha-Pinene | 0.92 | 0.94 | 0.99 | 1.00 |
| Beta-Pinene | 0.81 | 0.89 | 0.97 | 1.00 |
| Hexyl Acetate | 1.51 | 1.44 | 1.39 | 1.00 |
| Limonene | 0.77 | 0.87 | 1.02 | 1.00 |
| Dihydromyrcenol | 1.79 | 1.62 | 1.59 | 1.00 |
| Phenyl Ethyl Alcohol | 1.75 | 1.61 | 1.56 | 1.00 |
| Benzyl Acetate | 2.68 | 2.27 | 1.96 | 1.00 |
| Citronellol | 1.18 | 1.26 | 1.53 | 1.00 |
| Lilial | 0.98 | 1.11 | 1.47 | 1.00 |

The data in Table III reveals an increased bloom (impact) for hexyl acetate, dihydromyrcenol, phenyl ethyl alcohol, benzyl acetate, citronellol and lilial where fatty acid soap content ranges from 60 to at least 80% of total fatty acid materials. An almost fully neutralized condition as in Example 4 imparts less bloom to the aforementioned fragrance components. Contra results were found with the common fragrance components alpha-pinene, beta-pinene and limonene. Extent of neutralization had no effect with these components.

What is claimed is:

1. A personal care composition comprising:
   (i) from 0.00001 to 1% by weight of the composition of a fragrance component selected from the group consisting of hexyl acetate, dihydromyrcenol, phenyl ethyl alcohol, benzyl acetate and mixtures thereof; and
   (ii) from 1 to 30% of a $C_{10}$-$C_{24}$ fatty acid material by weight of the composition, wherein from 70 to 85% by weight of the fatty acid material is a salt and a remainder of the fatty acid material is a free fatty acid, and wherein the composition has a pH ranging from 7.7 to 8.5 and is a liquid with from 50 to 90% by weight water.

2. The composition according to claim 1 wherein the fragrance component is hexyl acetate.

3. The composition according to claim 1 wherein the fragrance component is dihydromyrcenol.

4. The composition according to claim 1 wherein the fragrance component is phenyl ethyl alcohol.

5. The composition according to claim 1 wherein the fragrance component is benzyl acetate.

6. The composition according to claim 1 wherein from 70 to 80% by weight of the fatty acid material is in salt form.

7. The composition according to claim 1 further comprising a structuring system of 0.01 to 10% of a starch and of 0.01 to 1% of a polyethyleneglycol having number average molecular weight from 1,000 to 100,000.

* * * * *